(12) United States Patent
Fujii et al.

(10) Patent No.: US 6,947,151 B2
(45) Date of Patent: Sep. 20, 2005

(54) SURFACE STATE INSPECTING METHOD AND SUBSTRATE INSPECTING APPARATUS

(75) Inventors: Yoshiki Fujii, Kyoto (JP); Kiyoshi Murakami, Fukuchiyama (JP)

(73) Assignee: OMRON Corporation, Kyoto (JP)

( * ) Notice: Subject to any disclaimer, the term of this patent is extended or adjusted under 35 U.S.C. 154(b) by 309 days.

(21) Appl. No.: 10/338,020

(22) Filed: Jan. 8, 2003

(65) Prior Publication Data

US 2003/0169418 A1 Sep. 11, 2003

(30) Foreign Application Priority Data

| Jan. 10, 2002 | (JP) | ................................. 2002-003449 |
| Dec. 16, 2002 | (JP) | ................................. 2002-364400 |

(51) Int. Cl.[7] ............................................. G01N 21/88
(52) U.S. Cl. ..................... 356/612; 382/150; 356/237.1; 356/237.5
(58) Field of Search .......................... 356/237.2–237.5, 356/237.1, 612–613; 382/150

(56) References Cited

U.S. PATENT DOCUMENTS

| 4,677,473 | A |   | 6/1987  | Okamoto et al. |
| 5,032,735 | A | * | 7/1991  | Kobayashi et al. ..... 250/559.34 |
| 5,039,868 | A | * | 8/1991  | Kobayashi et al. .......... 356/613 |
| 5,064,291 | A |   | 11/1991 | Reiser |
| 5,166,985 | A | * | 11/1992 | Takagi et al. ................ 382/150 |
| 5,245,671 | A | * | 9/1993  | Kobayashi et al. .......... 382/150 |
| 5,822,449 | A | * | 10/1998 | Kobayashi et al. .......... 382/141 |
| 6,023,663 | A | * | 2/2000  | Kim ........................... 382/150 |
| 6,040,895 | A | * | 3/2000  | Haas ........................... 356/399 |

FOREIGN PATENT DOCUMENTS

| JP | 62-127617 A | 6/1987 |
| JP | 6-1173 B2   | 1/1994 |

OTHER PUBLICATIONS

David W. Capson et al., "A Tiered–Color Illumination Approach for Machine Inspection of Solder Joints", IEEE Transactions on Pattern Analysis and Machine Intelligence, May 1988, pp. 387–393, vol. 10, No. 3, XP–002243987.

"Multiple–Image Vision Inspection Process", IBM Technical Disclosure Bulletin, Sep. 1987, pp. 1647–1649, vol. 30, No. 4, XP 000021763.

* cited by examiner

*Primary Examiner*—Richard A. Rosenberger
(74) *Attorney, Agent, or Firm*—Foley & Lardner LLP

(57) ABSTRACT

In a substrate inspecting apparatus comprising a projecting section (4) in which light sources (8), (9) and (10) are provided for emitting colored lights of R, G and B in directions having different elevation angles, one or two color components which is/are greater than the mean value of the intensities of color components is/are extracted for an inspecting region including a soldered portion. Inclined surfaces adapted to the light sources (8), (9) and (10) are converted into monochromatic shaded images by the extraction processing. A boundary position between the inclined surfaces adapted to the light sources (8) and (9) are converted into one shaded image having a mixed color of red and green and the boundary position between the inclined surfaces adapted to the light sources (9) and (10) is converted into a different shaded image.

7 Claims, 8 Drawing Sheets

SURFACE STATE INSPECTING METHOD AND SUBSTRATE INSPECTING APPARATUS

BACKGROUND OF THE INVENTION

1. Field of the Invention

The present invention relates to a technique for inspecting the surface state of a predetermined inspection object, for example, a curved face of a substance having a curved surface such as a soldered portion formed on a component mounting substrate, the inclination state of a component lead or the like.

2. Description of the Background Art

The applicant previously developed an apparatus for automatically inspecting a soldered portion on a substrate by an image processing method by utilizing the mirror reflecting property of the soldered portion (see the Patent Document 1).

[Patent Document 1]

Japanese Patent Publication No. 6-1173 (1994/1173)

FIG. 8 shows the structure of a substrate inspecting apparatus and the principle of an inspection which have been disclosed in the Patent Document 1. The inspecting apparatus serves to generate an image of an inspection object by three light sources 8, 9 and 10 for emitting lights having colors of red (R), green (G) and blue (B) and an image pick-up device 3, and the light sources 8, 9 and 10 are set such that an elevation angle formed with respect to a substrate surface is increased in order of R, G and B. On the other hand, the image pick-up device 3 is provided to pick up the image of a solder 2 to be an inspection object in a position placed just above.

The lights irradiated from the light sources 8, 9 and 10 are mirror reflected by the surface of the solder 2. In the optional position of the solder 2, a light emitted in a direction which is symmetrical with respect to the direction of the image pick-up device 3 seen from the same position is mirror reflected and is thereby guided to the image pick-up device 3. According to the optical system, therefore, a two-dimensional image having the colors R, G and B divided by the inclination of the solder surface is generated as shown in FIG. 9. In a spherical solder shown in the example, a flat surface in a central portion appears as a red image region, a steep surface in the vicinity of the substrate surface appears as a blue image region, and furthermore, a comparatively gentle inclined surface (moderate inclined surface) appears as a green image region. Based on the distribution state of the colors corresponding to the light sources, it is possible to decide the quality of the shape of the solder 2.

The inspection based on the principle described above is not restricted to a spherical solder but can also be applied to the inspection of the shape of a fillet. FIG. 10 shows the distribution state of the colors in the case in which the fillet on the substrate is observed by the optical system corresponding to the inclination state of the fillet. In FIG. 10, 50 denotes a substrate surface and S1 denotes a formation range of a land.

Also in the example of FIG. 10, the reflected light which is observed is divided, by the inclination angle of a solder, into blue on an upper steep surface, green on a middle steep surface and red on a surface which is almost flat in the vicinity of the substrate surface.

In the inspecting apparatus, a predetermined binary threshold is preset to each of the colors R, G and B. The image obtained by the image pick-up device 3 is changed into a binary value by the binary thresholds to extract a binary pattern for each of R, G and B (which will be hereinafter referred to as a "color pattern"). Referring to the color pattern, moreover, a pattern obtained in the image of a solder having an excellent shape is previously registered and the feature of each color pattern on the image of an inspection object is compared with that of the registered pattern, thereby deciding the quality of the surface state of the solder.

In a recent component mounting substrate, the size of a land is reduced with an increase in a density. In a small-sized substrate such as a substrate for a mobile telephone, particularly, the size of the land is to be reduced. However, when the size of the land is thus reduced, the inclination of the fillet is rapidly increased so that it is hard to extract each of the color patterns of R, G and B.

FIG. 11 shows an example of observation in the case in which the inclination of the fillet is very great. In this example, a formation range S2 of the land is reduced. Consequently, the fillet is inclined at an angle corresponding to the light source 10 for blue over a whole length so that most of a reflected light which is observed might be blue in some cases.

The same problem arises in the case in which the inclination of a component lead is to be observed. For example, in the case in which the upper surface of the lead is to be observed by using the optical system in FIG. 8, a very small change in an inclination angle which is caused by a float generated on the lead is included in a detection range of a normal red light. For this reason, it is hard to detect the very small float of the lead.

In the case in which the inclination state of an object having a very great inclination is to be observed in detail or the very small change of the inclination angle is to be detected, thus, it is hard to take measures in the optical system.

On the other hand, an increase in the number of the light sources can be proposed as a method of enhancing a resolution related to the detection of an inclined surface. In this case, a cost is increased.

SUMMARY OF THE INVENTION

In consideration of the problems, it is an object of the present invention to enhance a resolution related to the detection of an inclination angle by using the same optical system as that in the conventional art, to observe the inclination state of a steep surface in detail and to detect a fine change in an inclination of a predetermined inspection object such as a solder or a lead on a substrate with high precision, thereby enhancing precision in an inspection in the case in which the surface state of the inspection object is to be inspected.

A first surface state inspecting method according to the present invention comprises the steps of picking up an image of a light reflected from an inspection object under an illumination condition in which different colored lights are irradiated in a plurality of directions having different elevation angles with respect to the inspection object, selecting and executing a processing of extracting one color component having a maximum intensity in color components corresponding to the colored lights or a processing of extracting the color component having a maximum intensity and a color component having the second highest intensity for each pixel in an image region including an image of the inspection object based on a relationship between the intensities of the color components with respect to the image obtained by the image pick-up, and inspecting a surface state of the inspection object by using image data indicative of a result of the processing of extracting a color component in the image region.

The "inspection object" implies a curved surface or a surface having a predetermined inclination angle (including a horizontal surface), for example, a soldered portion on a substrate or a lead of a component. The colored lights irradiated in the directions having different elevation angles can have colors of red, green and blue, for example, and are not restricted thereto but two kinds of light sources such as red and green may be used.

The "image region including an image of the inspection object" can be set to be at least an image region cut out by the contour line of the image of the inspection object (that is, the image of the inspection object itself). Desirably, the same image region is set to be a rectangular region which is larger than the image of the inspection object.

Moreover, an image region including a plurality of objects can also be set to be the image region. Moreover, the whole image can be regarded as one image region to be processed.

The "color component corresponding to each colored light" can be supposed to be the feature amount of a color corresponding to each colored light irradiated in the directions. For example, in the case in which each of the colored lights of red, green and blue is to be irradiated, the intensity of each of color signals of red, green and blue can be regarded to be a color component. For a digital image, the intensity of each color signal can be expressed by a gradation for each pixel.

In the processing of extracting a color component, it is possible to determine to extract only one color component having a maximum intensity or two color components having the color component having a maximum intensity and a color component having the second highest intensity depending on a difference in the intensity between the first color component and the second color component, for example. More specifically, it is preferable that only the first color component should be extracted if the first and second color components make a difference in the intensity which is equal to or greater than a predetermined value, and the first and second color components should be extracted if their difference is smaller than the predetermined value.

The principle of the processing of extracting a color component according to the present invention will be described by taking an optical system shown in FIG. 8 as an example. In the following description, an inclined surface having such an inclination that a mirror reflected light for an irradiated light is incident on an image pick-up device when the light is irradiated from a predetermined light source onto an inspection object will be referred to as "an inclined surface adapted to a light source". Moreover, two light sources (light sources 8 and 9, and 9 and 10 in FIG. 8) provided without interposing other light sources therebetween will be referred to as "adjacent light sources" and lights emitted from these light sources will be referred to as "lights emitted in directions having adjacent elevation angles". In addition, an inclined surface provided in a transition from the inclined surface adapted to one of the adjacent light sources to the inclined surface adapted to the other light source will be referred to as "an inclined surface in a boundary position".

In the case in which the inclined surface of the inspection object is adapted to a predetermined light source, a color component corresponding to the same light source is supposed to be much more superior to other color components. Therefore, it is possible to obtain an image having the same color as that of the light emitted from the light source by extracting a color component having the highest intensity. Referring to the inclined surface in the boundary position between the inclined surfaces adapted to the adjacent light sources, moreover, it is supposed that the intensities of the color components corresponding to the adjacent light sources are close to each other. Consequently, it is possible to obtain an image having a mixed color of the colors corresponding to the adjacent light sources by extracting a color component having a maximum intensity and a color component having the second highest intensity.

For example, in the case in which observation is to be carried out by the optical system in FIG. 8, the inclined surfaces adapted in the direction of the arrangement of the light sources 8, 9 and 10 can be expressed by the colors of red, green and blue, respectively. Furthermore, an inclined surface in the boundary position for the light sources 8 and 9 can be expressed by a mixed color of red and green, and an inclined surface between the light sources 9 and 10 can be expressed by a mixed color of green and blue. In addition to the colors corresponding to the light sources, thus, it is possible to express the inclined surface by the mixed color of the colors corresponding to the adjacent light sources. Consequently, a resolution related to the detection of an inclination angle can be set more finely based on the distribution state of each color on an image than that in the conventional art.

By the same optical system as that in the conventional art, accordingly, the inclination angle of the surface of the inspection object can be recognized with the same resolution as that of the case in which more light sources are provided. Thus, it is possible to enhance precision in an inspection by dividing and identifying a steep surface by the inclination angle or detecting a fine change in the angle.

In the case in which an image is to be displayed after the processing of extracting a color component, moreover, it is possible to display an image having a clear color by one or two color components. Also in the case in which the surface of the inspection object has a slight diffusing property, accordingly, a predetermined color component corresponding to an inclination angle is extracted. Consequently, the surface state of the inspection object can be expressed clearly and the suitability of the surface state can be decided easily over a display screen.

As shown in FIG. 8, furthermore, in the case in which colored lights of red, green and blue are to be irradiated, the step of executing the processing of extracting a color component can include the step of obtaining the mean value of the intensities of the color components and the step of extracting one or two color components which are greater than the mean value in the color components.

For example, in the optical system having the structure shown in FIG. 8, a red component in the image of the inclined surface adapted to the light source 8 for red is overwhelmingly superior to the color components of green and blue. For this reason, only the red component is greater than the mean value of the intensities of the color components. On the other hand, in the boundary position between the inclined surfaces adapted to the light sources 8 and 9, a difference in the intensity between the red component and the green component is reduced and the blue component is maintained to be small. Therefore, the red and green components are greater than the mean value of the color components. Accordingly, it is possible to extract one or two color components depending on the inclination angle of the inclined surface corresponding to a noticed pixel by calculating the mean value of the color components and removing the color component which is less than the mean value for each pixel.

In the processing described above, it is desirable that a pixel having a lower mean value than a predetermined value (that is, a pixel having a low luminousity) should be considered to correspond to a portion in which a sufficient reflection cannot be obtained and should be thereby excluded from the object of the extraction processing.

Next, the step of inspecting a surface state of the inspection object can include the step of grouping each pixel in the region based on a type and combination of an extracted color component in the pixel region after executing the step of the processing of extracting a color component, and the step of deciding a suitability of the surface state of the inspection object based on a distribution state of a pixel belonging to each group.

In the grouping step, a group can be set for each color component and each combination of two color components corresponding to lights emitted in the directions having the adjacent elevation angles. A pixel from which only a single color component is extracted is included in the image region of an inclined surface displayed in a color corresponding to the extracted color component. Moreover, a pixel from which two color components are extracted is included in the image region of an inclined surface displayed by a mixed color of the colors corresponding to the extracted color components.

According to the grouping processing, thus, the surface state of the inspection object can be divided and detected into inclined surfaces corresponding to the number of groups. When the inclination state of the inclined surface is changed, the result obtained by the processing of extracting a color component is varied and the result of the grouping is also changed. As a result, the distribution state of a pixel belonging to each group can also be varied.

The distribution state of the pixel belonging to each group can be extracted by a labeling processing for attaching different labels for each group to each pixel, for example. In this case, it is possible to divide and recognize an image region corresponding to each group based on the result of the labeling.

If the distribution state of each group is changed, moreover, the number of pixels belonging to each group is also changed spontaneously. Therefore, the number of pixels in each group can also be set to be a parameter indicative of the distribution state of the pixels belonging to the groups.

At the step of deciding a suitability of a surface state of the inspection object, it is possible to decide the suitability by comparing, with a predetermined reference value, a feature amount (a position of a center of gravity, an area or the like) for each group extracted by the labeling processing or a parameter such as the number of pixels. It is desirable that the feature amount or the parameter for an excellent surface state should be previously calculated by using the image of a model of the inspection object or the like and the reference value should be set based on a value indicative of a result of the calculation.

According to the grouping processing and the decision processing described above, the inclined surfaces adapted to the light sources and the inclined surface in their boundary position can be divided and detected based on the distribution state of a pixel belonging to each group. Consequently, the suitability of the surface state of the object can be decided easily with high precision.

Furthermore, a second surface state inspecting method according to the present invention comprises the steps of picking up an image of a light reflected from an inspection object under an illumination condition in which different colored lights are irradiated in a plurality of directions having different elevation angles with respect to the inspection object, comparing a color component corresponding to a predetermined colored light with a plurality of thresholds set stepwise for each pixel in an image region including an image of the inspection object for the image obtained by the image pick-up, and inspecting a surface state of the inspection object depending on a result of the comparison in the pixel.

By way of example, according to the optical system shown in FIG. 8, the intensity of the color component corresponding to the same color (for example, blue) is changed depending on an inclination angle also in an inclined surface which can be extracted with the color. Accordingly, if a plurality of thresholds are set to the same color component, the angle of the inclined surface can be divided and detected more finely so that a retrieval can be carried out in more detail. Also in the case in which a change in an angle such as the float of a lead is to be detected, moreover, it is possible to detect a very small change in the angle, thereby enhancing precision in the inspection.

A first substrate inspecting apparatus according to the present invention comprises illuminating means having a plurality of light sources for emitting different colored lights which are provided in directions of different elevation angles with respect to a substrate to be an inspection object respectively, image pick-up means for picking up an image of a light reflected from the substrate, image input means for fetching an image generated by the image pick-up means in a state in which each of the light sources of the illuminating means is turned on, color component extracting means for selecting and executing a processing of extracting one color component having a maximum intensity in color components corresponding to the light sources or a processing of extracting the color component having a maximum intensity and a color component having the second highest intensity based on a relationship of an intensity of each color component for each pixel in an image region including an image of the inspection object with respect to the input image fetched by the image input means, deciding means for deciding a suitability of a surface state of the inspection object by using image data in the image region after executing the processing by the color component extracting means, and output means for outputting a result of the decision carried out by the deciding means.

The illuminating means can be provided with a ring-shaped light source having different diameters for each color, for example. Moreover, one light source can be constituted by a luminous body group having a plurality of luminous bodies arranged like a ring, for example, an LED. Furthermore, a luminous body group having the same color can be arranged concentrically in a plurality of stages, thereby constituting one light source.

The image pick-up means can be constituted by a CCD camera capable of generating an image signal for each color. The image input means is incorporated in a computer for carrying out an image processing for an inspection and serves to generate an image to be a processing object, and can include an amplifying circuit for amplifying an image signal sent from the image pick-up means and an A/D converting circuit for generating a digital image for a processing.

The image pick-up means is not restricted to a device for generating an analog image signal but may be a digital camera. In this case, the image input means can be constituted as an input port for individually fetching digital image data for each color.

The color component extracting means and the deciding means can be constituted by a computer setting a program for performing the step of executing the color component extraction processing and the step of inspecting the surface state of the inspection object, respectively. The memory of the computer can store image data obtained after the processing of extracting the image data and color component of a processing object in addition to the program.

Moreover, image regions to be the processing objects of the color component extracting means and the deciding means can be preset based on a substrate having a good mounting condition and the position and size of the inspection object which are obtained from the design data of the substrate. Alternatively, an image obtained by the image pick-up means may be displayed and the designation of an image region corresponding to each inspection object may be accepted over a display screen and may be stored in the memory. The whole image includes only one inspection object. If the inspection object appears sufficiently largely over the image, the whole image can also be set to be the image region of a processing object.

The output means can be constituted as an interface circuit for outputting a result of the decision obtained by the deciding means to an external device. Moreover, means for displaying the result of the decision or information storage means for storing the result of the decision in a predetermined storage medium can be used as the output means (also in a third substrate inspecting apparatus which will be described below).

According to the apparatus having the structure described above, it is possible to more finely detect an inclination angle and automatically decide the suitability of a surface state for a surface such as a solder on a substrate or a lead of a component based on the first method. Consequently, it is possible to carry out an inspection in more detail with the same hardware structure as that in the conventional art and to provide an automatic substrate inspecting apparatus having a high performance without increasing a cost.

In a preferred embodiment of the substrate inspecting apparatus, the illuminating means includes three kinds of light sources for emitting colored lights of red, green and blue. Moreover, the color component extracting means includes means for calculating a mean value of the intensities of the color components corresponding to the light sources and means for extracting one or two color components which is/are greater than the mean value thus calculated.

According to such a structure, the feature amount of each of the color signals of R, G and B constituting a color image can be set to be a color component corresponding to each light source. Therefore, the processing of extracting each component can easily be carried out. Moreover, a color component which is greater than the mean value of the intensities of the color components is extracted for each pixel. Consequently, it is possible to extract inclined surfaces adapted to the direction of arrangement of light sources by the same color as a light emitted from the light source, and furthermore, an inclined surface in a boundary position between the inclined surfaces by a mixed color of colors of two corresponding light sources, respectively.

In an apparatus according to a further preferred embodiment, the deciding means includes means for grouping each pixel in the image region based on a type and combination of the extracted color component after the processing of the color component extracting means, thereby deciding a suitability of a surface state of the inspection object based on a distribution state of a pixel belonging to each group. As described above, if each pixel in the inspection region is grouped based on the type and combination of a color component, the inclined surfaces adapted to the light sources and the inclined surface in their boundary position can be divided and detected. Accordingly, the surface of the inspection object can be divided automatically with resolutions which are greater than the number of the light sources, and the quality of the inclination state can be decided with high precision.

A second substrate inspecting apparatus according to the present invention comprises display means for displaying an image based on each color component extracted by the color component extracting means and input means for accepting the input of data indicative of a result of the decision of the quality for an image displayed by the display means in addition to the same illuminating means, image pick-up means, image input means and color component extracting means as those in the first substrate inspecting apparatus.

An image region to be the processing object of the color component extracting means may be designated optionally or a preset image region may be an object.

The display means is constituted by a monitor device for displaying an image or display control means for the monitor device. The display control means can be constituted by a computer incorporating a program for display control. The input means can be constituted by an apparatus for an input operation such as a mouse, a keyboard, a console and the like. Data input by the input means can be output to an external device or the like and can be stored in a predetermined storage medium.

The substrate inspecting apparatus having the second structure relates to a visual inspecting apparatus in which a user decides the quality of an inspection object while confirming a displayed image and inputs a result of the decision. In the apparatus, it is possible to display an image having the resolution of an inclination angle enhanced by colors corresponding to the light sources and a mixed color of the colors for a substrate to be an inspection object. Consequently, the surface state of the object can be observed in more detail by the same illuminating system as that of the conventional art. Thus, it is possible to carry out an inspection with high precision.

Moreover, a third substrate inspecting apparatus according to the present invention comprises the same illuminating means, image pick-up means and image input means as those of the first and second apparatuses, and furthermore, comparing means for comparing a color component corresponding to a predetermined light source with a plurality of thresholds set stepwise for each pixel in an image region including the image of an inspection object with respect to an input image fetched by the image input means, deciding means for deciding the suitability of a surface state of the inspection object by using a result of the comparison in the pixel, and output means for outputting a result of the decision obtained by the deciding means. It is desirable that the comparing means and the deciding means should be constituted by a computer setting a program for executing the processings of the respective means.

In the same manner as the first substrate inspecting apparatus, the third substrate inspecting apparatus serves to automatically decide the suitability of the surface state of the inspection object. According to the apparatus having the structure, the inclination angle of the inclined surface detected as the same color pattern can be decided and detected in detail with a plurality of thresholds. Accordingly, a fillet having a great inclination shown in FIG. 11 and a very small float of a lead can also be detected with high precision so that precision in the decision can be enhanced. In addition, the same hardware structure as that of the conventional art can be employed. Consequently, it is possible to provide an automatic substrate inspecting apparatus having a high performance without increasing a cost.

DETAILED DESCRIPTION OF PREFERRED EMBODIMENTS

Figure 1:
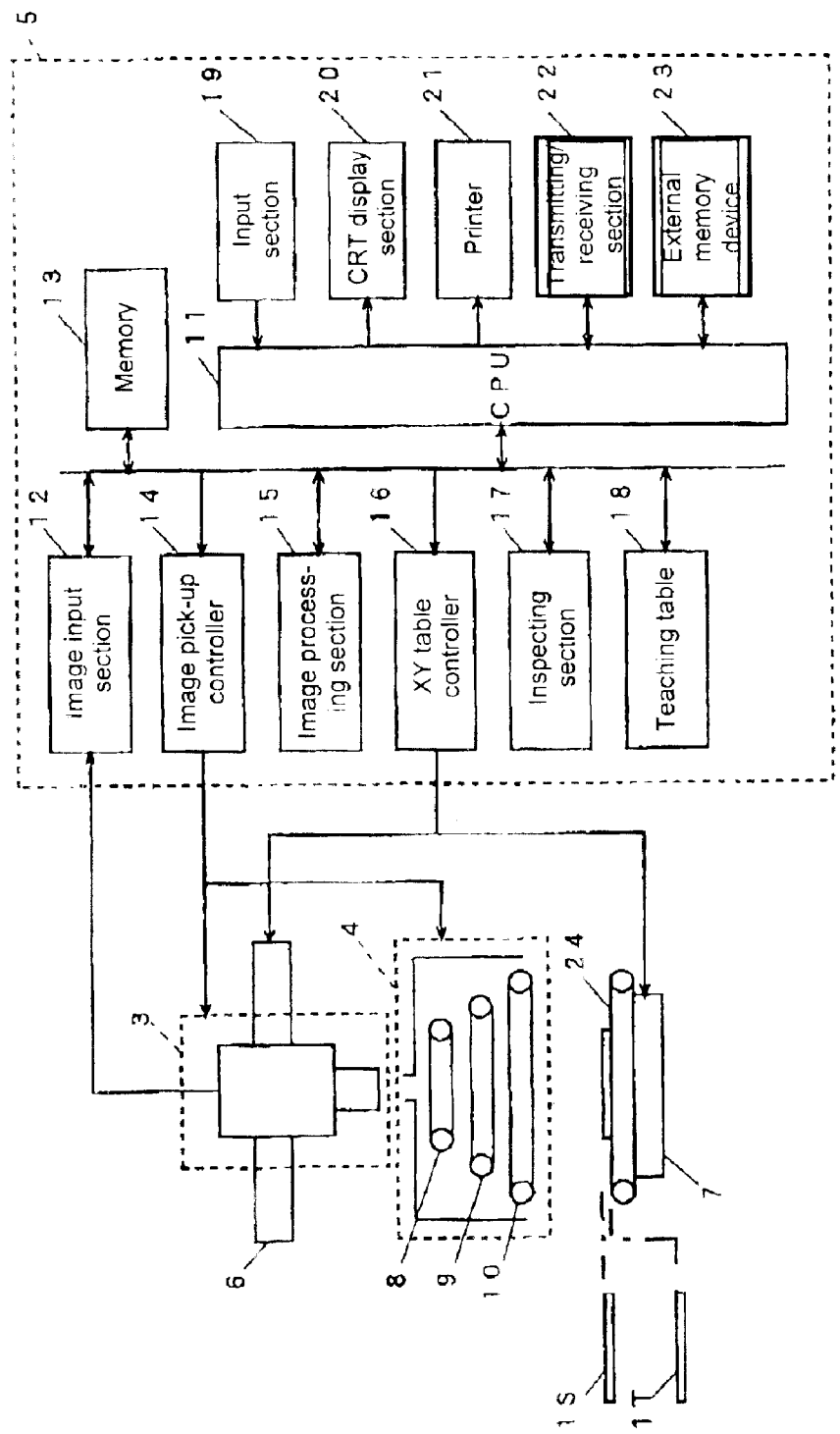
FIG. 1 is a block diagram showing the structure of a substrate inspecting apparatus according to an embodiment of the present invention.

FIG. 1 shows the structure of a substrate inspecting apparatus according to an embodiment of the present invention.

The substrate inspecting apparatus serves to process an image picked up from a substrate to be an inspection object and to decide the quality of a soldered portion on the substrate or the like, and is constituted by an image pick-up section 3, a projecting section 4, a control section 5, an X-axis table section 6, a Y-axis table section 7 and the like.

In FIG. 1, 1T denotes the substrate to be the inspection object (which will be hereinafter referred to as an "inspected substrate 1T"). Moreover, 1S denotes a reference substrate in which a soldering state and a component mounting state are excellent, which is used during teaching prior to an inspection.

The Y-axis table section 7 includes a conveyer 24 for supporting the substrates 1S and 1T, and moves the conveyer 24 by means of a motor which is not shown to move the substrates 1S and 1T in a Y-axis direction (a direction orthogonal to the paper of FIG. 1). The X-axis table section 6 moves the image pick-up section 3 and the projecting section 4 above the Y-axis table section 7 in an X-axis direction (a transverse direction in the drawing) while supporting them.

The projecting section 4 is constituted by three circular light sources 8, 9 and 10 having different diameters. The light sources 8, 9 and 10 serve to emit red, green and blue lights respectively, and are provided to be positioned in directions corresponding to different elevation angles as seen from the support surfaces of the substrates 1S and 1T with centers aligned with a position placed just above an observation position.

The image pick-up section 3 is a CCD camera for generating a color image, and is positioned such that an optical axis thereof corresponds to the centers of the light sources 8, 9 and 10 in a vertical direction. Consequently, a light reflected by the substrates 1S and 1T to be an observation object is incident on the image pick-up section 3 and is converted into a color image signal for each of primaries R, G and B, and the color image signal is input to the control section 5.

The control section 5 is a computer comprising a CPU 11 as a main control body, and is constituted by an image input section 12, a memory 13, an image pick-up controller 14, an image processing section 15, an XY table controller 16, an inspecting section 17, a teaching table 18, an input section 19, a CRT display section 20, a printer 21, a transmitting/receiving section 22, an external memory device 23 and the like.

The image input section 12 comprises an amplifying circuit for amplifying each of image signals of R, G and B sent from the image pick-up section 3, an A/D converting circuit for converting the image signals into digital signals, and the like. The memory 13 sets an image storage area for storing shaded image data on a digital amount for each of R, G and B, a binary image obtained by changing the shaded images into binary values and the like.

The image pick-up controller 14 comprises an interface for connecting the image pick-up section 3 and the projecting section 4 to the CPU 11 and the like, and controls to regulate the amount of light of each light source in the projecting section 4 based on an instruction sent from the CPU 11 and to maintain the mutual balance of each colored light output of the image pick-up section 3.

The XY table controller 16 includes an interface for connecting the X-axis table section 6 and the Y-axis table section 7 to the CPU 11 and the like, and controls the moving operations of the X-axis table section 6 and the Y-axis table section 7 based on an instruction sent from the CPU 11.

The teaching table 18 stores decision files collecting inspection information such as the set position and size of an inspection region, a binary threshold required for extracting a color pattern for an inspection in the inspection region, the feature amount (the position and size of the color pattern and the like) thus extracted, the number of pixels for each color group which will be described below, a reference value for a quality decision and the like for various substrates. These decision files are taught by a person in charge with the use of an image obtained by picking up the image of the reference substrate IS prior to an inspection, are read from the CPU 11 and are set to the memory 13 or the like during the inspection, and are supplied to the image processing section 15, the inspecting section 17 and the like.

The image processing section 15 extracts each gradation of R, G and B and a luminousity expressed by the sum of the gradations on a pixel unit from each pixel data of R, G and B stored in the memory 13. Furthermore, the image processing section 15 executes, for each inspection region, a processing of extracting each color component, an addition processing for each color group and the like which will be described below for a soldered portion, a processing of extracting each color pattern of R, G and B, and a processing of calculating the feature amount of the color pattern thus extracted for portions other than the soldered portion.

The inspecting section 17 receives the supply of a decision reference value or the like from the teaching table 18 and compares the number of pixels for each group obtained by the image processing section 15 or the feature amount of each color pattern with the decision reference value to carry out a quality decision and outputs the result of the decision to the CPU 11. The CPU 11 synthesizes the result of the decision for each inspection region and decides whether the inspected substrate 1T is an excellent product or not. The final result of the decision is output to the CRT display section 20, the printer 21 or the transmitting/receiving section 22.

The input section 19 serves to input various conditions and inspection information for an inspection and is constituted by a keyboard, a mouse and the like. The CRT display section 20 (which will be hereinafter referred to as a "display section 20") receives, from the CPU 11, the supply of image data, the result of an inspection and the data input from the input section 19 and displays them on a display screen. Moreover, the printer 21 receives the supply of the result of the inspection and the like from the CPU 11 and prints out the same result in a predetermined format.

The transmitting/receiving section 22 serves to transfer data together with other devices such as a component mounting machine, a soldering device and the like, and can transmit identification information and the contents of a defect to a correcting device in a second stage for the inspected substrate 1T decided to be defective, thereby quickly correcting a defective portion, for example. The external memory device 23 serves to read and write data to a storage medium such as a flexible disk or a magneto-optical disk and is used for storing the result of the inspection and fetching a program required for the inspection and set data from the outside.

In the structure described above, the image processing section 15 and the inspecting section 17 are constituted by a special processor incorporating a program for executing each processing. The special processor does not need to be always provided but the functions of the image processing section 15 and the inspecting section 17 may be given to the CPU 11 for carrying out a main control.

In the substrate inspecting apparatus according to the present embodiment, in the case in which a soldered portion is to be inspected, the inclination angle of a soldered surface is divided finer for detection than that in the conventional art, thereby carrying out an inspection with high precision.

Figure 2:
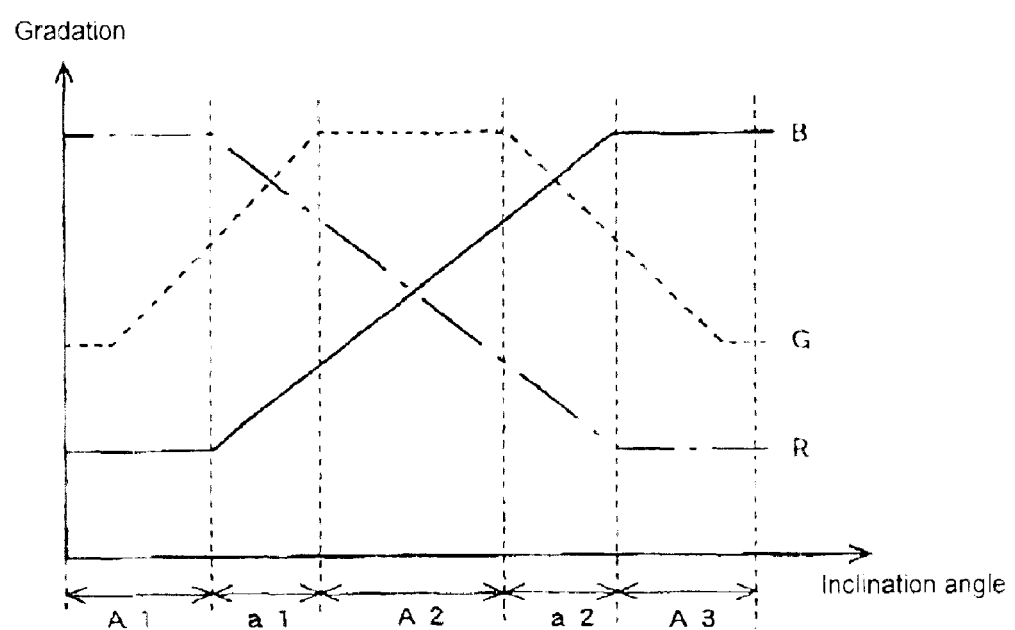
FIG. 2 is a graph showing the relationship between an inclination angle of a solder surface and a gradation of each color component.

FIG. 2 typically shows the state of a change in the gradation of each color component of red (R), green (G) and blue (B) which is obtained by a change in the inclination angle of the soldered surface for an image obtained by the optical system in FIG. 1. Herein, the inclination angle is the angle of the soldered surface formed in a horizontal direction and has a smaller value as the soldered surface becomes more horizontal.

According to the optical system shown in FIG. 1, the red component is superior to other color components within an angle range A1 which is almost flat, and is reduced when the inclination angle is increased. To the contrary, the blue component is increased when the inclination angle is increased, and is superior to the other color components within an angle range A3 indicative of a steep soldered surface. The green component is superior within an angle range A2 corresponding to a gentle inclined surface (a moderate inclined surface) between the angle ranges A1 and A3. In the other angle ranges, moreover, when the angle of the soldered surface is more increased when the angle range A2 is closer.

Within an angle range a1 for a transition from the angle range A1 to the angle range A2, the green component to be increased gradually approaches the red component to be decreased, and furthermore, their relationship is reversed to increase a difference. Also within an angle range a2 for a transition from the angle range A2 to the angle range A3, the blue component to be increased gradually approaches the green component to be decreased, and furthermore, their relationship is reversed to increase a difference.

In the present embodiment, the largest color component or the largest color component and the second largest color component is/are extracted for each pixel in the inspection region based on the above-mentioned characteristic. Consequently, the soldered surfaces corresponding to the five angle ranges A1, A2, A3, a1 and a2 are divided and extracted.

The processing of extracting the color components is carried out on the basis of a mean value of each color component. As shown in FIG. 2, a single color component corresponding to each of the light sources 8, 9 and 10 is superior to two other color components within the angle ranges A1, A2 and A3 adapted to the light sources 8, 9 and 10. In this case, if the mean values of the three color components are obtained, they are increased by one superior color component. For this reason, the mean value is positioned between the superior color component and two other inferior color components.

On the other hand, within the angle ranges a1 and a2 corresponding to the inclined surface in a boundary position, a difference between the largest color component and the second largest color component is reduced. In addition, a great difference is made between the two color components and the residual color component. For this reason, the mean value of the three color components is positioned between the second largest color component and the residual inferior color components.

Figure 3:
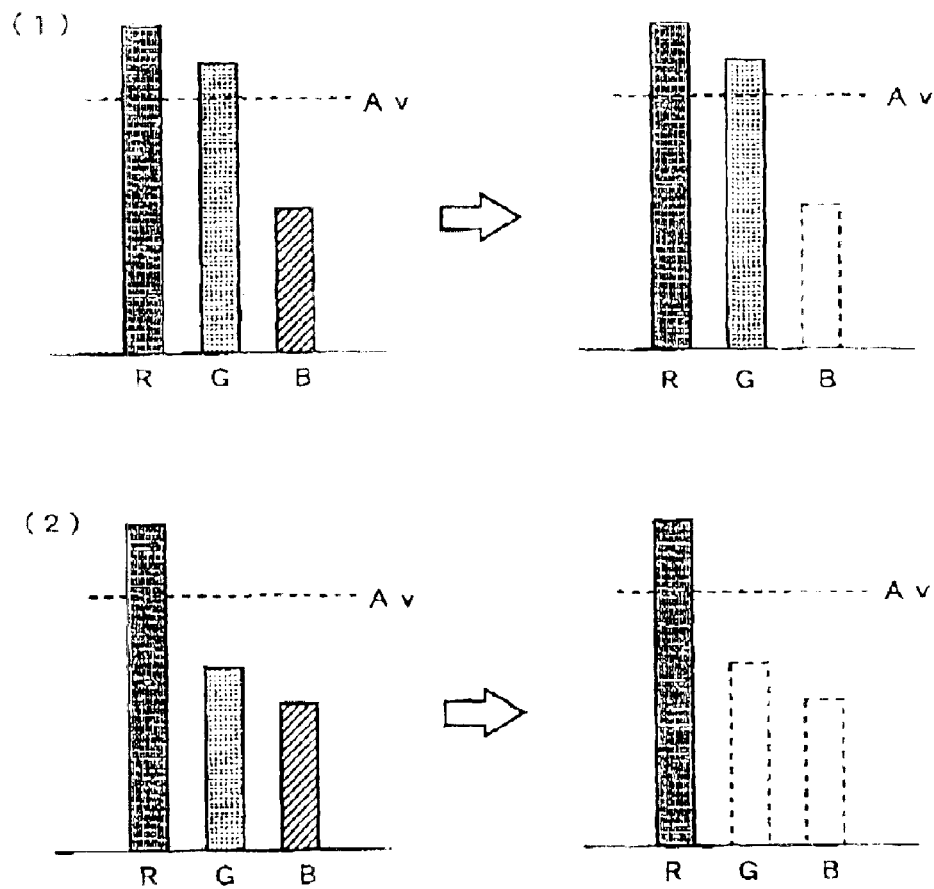
FIG. 3 is an explanatory diagram showing a method of extracting the color component.

FIG. 3 shows a specific example of the processing of extracting a color component.

FIG. 3(1) shows a processing for one pixel in the angle range a1 in FIG. 2. In the illustrated example, the color components of red and green have high gradations. Therefore, only the blue component has a lower gradation than the mean value Av of each gradation. In this case, the gradations of the color components of red and green are maintained, while the gradation of the blue component is changed to zero.

FIG. 3(2) shows a processing for one pixel in the angle range A1 in FIG. 2. In the illustrated example, the gradation of the red component is higher than two other components, and furthermore, a difference in a gradation between the color components of green and blue is small. Therefore, only the red component has a higher gradation than the mean value Av. In this case, only the gradation of the red component is maintained, while the gradations of the green and blue components are changed to zero.

Referring to the other angle ranges, similarly, only the gradation of the green component is maintained within the angle range A2 and only the gradation of the blue component is maintained within the angle range A3, and the gradations of two other components are changed to zero. Within the angle range a2, moreover, the gradations of the color components of green and blue are maintained and the gradation of the red component is changed to zero.

By such a processing, the inclined surfaces corresponding to the angle ranges A1, A2 and A3 are converted into monochromatic shaded images of red, green and blue, respectively. Moreover, the inclined surface corresponding to the angle range a1 is converted into a shaded image having a mixed color of red and green and the inclined surface corresponding to the angle range a2 is converted into a shaded image having a mixed color of green and blue.

Figure 4:
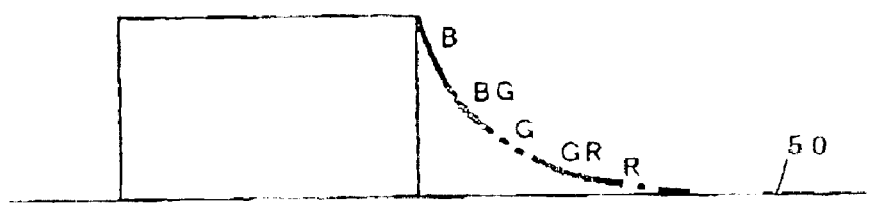
FIG. 4 is an explanatory view showing a state in which an inclined surface is divided by five color regions.

FIG. 4 typically shows a color distribution appearing on an image after the execution of the processing of extracting the color component for a fillet on a substrate corresponding to the inclination state of the fillet. The inclination angle of the fillet in the illustrated example is changed to be gradually decreased from an angle corresponding to the angle range A3 shown in FIG. 2 and to be flat in a position provided in contact with a substrate surface. Consequently, the color regions of blue (B), a mixed color of blue and green (indicated as BG in the drawing), green (G), a mixed color of green and red (indicated as GR in the drawing) and red (R) sequentially appear in such a direction that the inclination angle is decreased. In the color regions of the mixed colors BG and GR, a tone of color is changed depending on the ratio of the intensities of two kinds of color components constituting the mixed color.

According to the processing of extracting the color component, thus, each pixel constituting the image of a soldered surface can be grouped into the five kinds of color regions depending on the type and combination of the color components thus extracted (five kinds of groups corresponding to the color regions will be hereinafter referred to as "color groups").

According to the five kinds of color groups, the appearance frequencies of the five kinds of colors on an image can be indicated with the number of pixels belonging to each color group. As shown in FIG. 4, the five kinds of colors indicate the distribution state corresponding to the inclination angle of the soldered surface. If the inclination state of the soldered surface is changed so that the distribution state of each color is varied, therefore, it is a matter of course that the appearance frequency of each color is also changed. More specifically, the number of pixels for each color group can be regarded to be a parameter indicative of the distribution state of the five kinds of colors on the image. For this reason, it is possible to decide the quality of the inclination state of the soldered surface with the number of pixels.

In the substrate inspecting apparatus according to the present embodiment, referring to the soldered portion on the inspected substrate 1T, a single color component or two color components is/are extracted for each pixel in an inspection region which is set by the method shown in FIG. 3, and each pixel is classified into the five kinds of color groups based on the type and combination of the color component thus extracted and the number of pixels included in each group is obtained for each color group. By a comparison of the number of pixels for each color group with a decision reference value, furthermore, the quality of the soldered portion is decided.

A detailed procedure in teaching for an inspection and the inspection will be sequentially described below.

Figure 5:
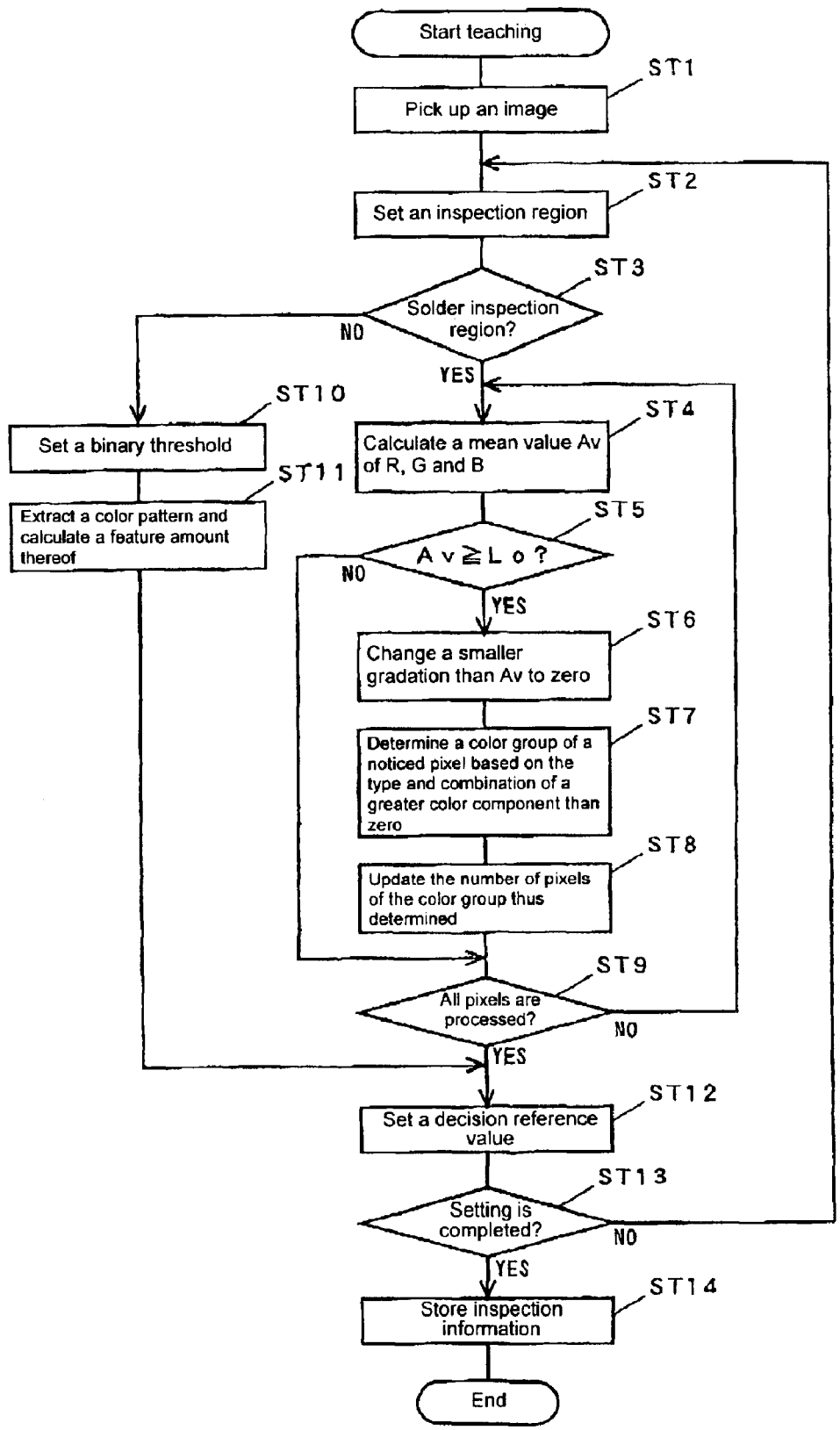
FIG. 5 is a flowchart showing a procedure for teaching.

FIG. 5 shows a procedure during the teaching. In FIG. 5 and the following description, a step in each processing is indicated as "ST".

During the teaching, first of all, a person in charge operates the input section 19 to register the name and size of a substrate to be a teaching object and the like, and then sets the reference substrate 1S on the Y-axis table section 7 and starts to pick up an image under an illumination by the projecting section 4 (ST1). By this processing, image signals of R, G and B are fetched into the image input section 12 and a digital conversion processing is then carried out, and color shaded image data on a processing object are input into the memory 13. Moreover, a color image thus input is displayed on the display section 20.

The person in charge positions the image pick-up section 3 and the projecting section 4 in a predetermined inspected portion and picks up an image, and specifies an inspection region for the obtained image by using a mouse or the like. In response to the specifying operation, the CPU 11 proceeds to a step ST2 in which the set position and size of the inspection region are fetched and temporarily stored in the memory 13 (ST2).

On the other hand, in the case in which the inspection region includes the soldered portion, the person in charge inputs identification information indicative of the purport subsequently to the operation for setting the inspection region. When the input of the identification information gives a decision of "YES" at a step ST3, the processings of steps ST4 to ST8 are executed by sequentially paying attention to a pixel in the set inspection region.

At the step ST4, the mean value Av of each gradation of R, G and B is calculated for one pixel in the inspection region. At the subsequent step ST5, the mean value Av is compared with a predetermined value L0. The threshold L0 is set based on an average brightness of an image in the soldered portion. In the case in which the mean value Av is smaller than a threshold L0, therefore, a decision of "NO" is obtained at the step ST5. In this case, the following steps STs 6, 7 and 8 are skipped to end a processing for a pixel to which attention is paid.

If the mean value Av is equal to or greater than the threshold L0, a decision of "YES" is obtained at the step ST5. At the next step ST6, a smaller gradation than the mean value Av in the gradations of R, G and B is changed to zero.

At the step ST7, next, a color group to which the noticed pixel belongs is determined based on the gradation of each color component after the processing of the step ST6. In the case in which one color component has a higher gradation than zero in the noticed pixel, a color group corresponding to a color (any of R, G and B) represented by the single color component is set to be an assignment group. In the case in which two color components have higher gradations than zero, moreover, a color group corresponding to a mixed color (RG or GB) corresponding to the two kinds of color components is set to be the assignment group.

When the assignment group of the noticed pixel is thus determined, the number of pixels of each group which is determined is updated to a value obtained by adding one to a current value at the next step ST8. The initial number of pixels is set to be zero.

Subsequently, the same processing is executed for each pixel in the inspection region. Consequently, it is possible to obtain the number of pixels belonging to each color group of R, G, B, RG and GB in the inspection region.

When the processings for all the pixels in the inspection region are completed, a decision of "YES" is obtained at a step ST9 and the processing proceeds to a step ST12 in which a decision reference value is set based on the number of pixels obtained finally for each color group. It is desirable that the decision reference value should be smaller corresponding to a predetermined margin than the final number of pixels (for example, a value corresponding to 90% of the final number of pixels and the like).

On the other hand, in the case in which the inspection region is set to a portion other than the soldered portion at the step ST2, a decision of "NO" is obtained at the step ST3. At steps ST10 and ST11, data for an inspection using the color patterns of R, G and B are set in the same manner as in the conventional art. At the step ST10, the person in charge inputs a binary threshold for each of R, G and B by a method of specifying a position having an optimum density on the image of the display section 20. The CPU 11 fetches the set value and stores the same set value in the memory 13 corresponding to the set data (position and size) of the inspection region.

At the step ST11, furthermore, each color pattern is extracted based on the binary threshold thus set. Referring to the color pattern, feature amounts such as the position of a center of gravity, an area and the like are calculated. Then, the processing proceeds to a step ST12 in which a decision reference value for a quality decision is set based on the feature amounts.

In the same manner, subsequently, the image of the inspected portion on the substrate is sequentially picked up and the inspection region is set. Then, the pixel in the inspection region is classified into the five kinds of color groups to obtain the number of the pixels for each group in the soldered portion and the color patterns of R, G and B are extracted to obtain the feature amounts in portions other than the soldered portion. A decision reference value for deciding quality related to the inspection region is set based on the number of the pixels and the feature amount which are thus obtained. Inspection information causing the decision reference value to correspond to the set data in that region (including the binary threshold of each color pattern in a non-soldered portion) is created for the inspection region and is temporarily stored in the memory 13.

When all the non-inspected portions are completely set, a decision of "YES" is obtained at a step ST13. At a step ST14, a decision data file is created based on the inspection information stored temporarily in the memory 13 for each non-inspected portion and is stored in the teaching table 18. Referring to the decision data file, a flag for identification is set to the inspection region specified as the inspection region of the soldered portion.

Figure 6:
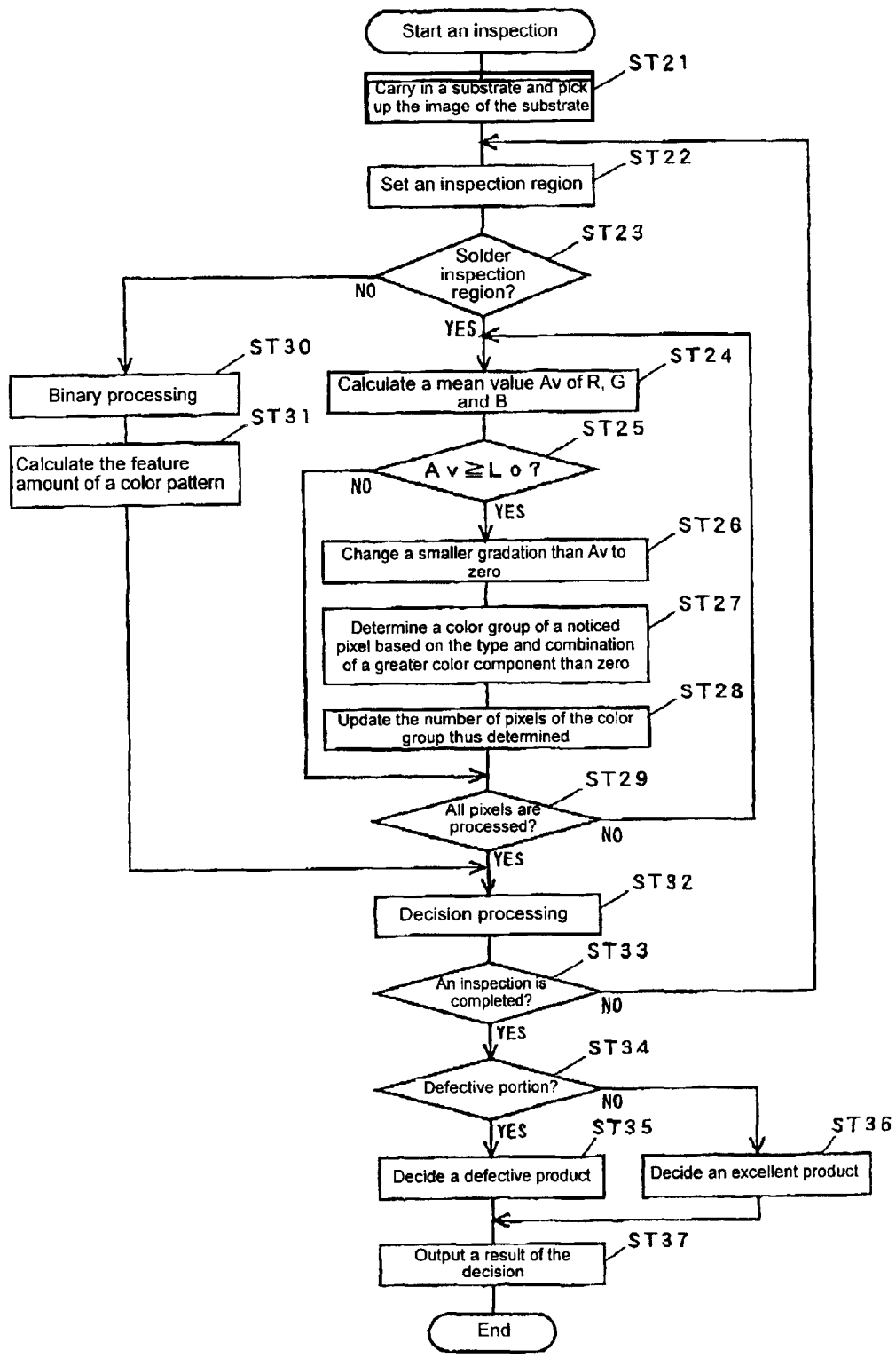
FIG. 6 is a flowchart showing a procedure for an inspection.

FIG. 6 shows a procedure for an automatic inspection in the substrate inspecting apparatus. In FIG. 6, the steps are indicated by ST21 and subsequent designations. Moreover, the procedure in FIG. 6 is carried out over one substrate and is repeated corresponding to the number of the inspected substrates.

Prior to the inspection, the person in charge specifies the type of the inspected substrate 1T based on the name of the substrate or the like. The CPU 11 reads a decision data file corresponding to the inspected substrate 1T through the teaching table 18 according to the specification and sets the same decision data file in the memory.13. When an inspection starting operation is carried out under this condition, the inspected substrate 1T is delivered into the Y-axis table section 7 to start image pick-up at the first step ST21.

Next, the CPU 11 positions the image pick-up section 3 and the projecting section 4 in an initial inspected portion based on the set data of the inspection region in the decision data file, generates the image of the inspected portion and sets the inspection region on the image (ST22). In the case in which the flag for identification is set to the inspection region, a decision of "YES" is obtained at a step ST23. By sequentially paying attention to each pixel in the inspection region, the same processings as those in the steps ST4 to ST8 during the teaching are executed. Consequently, each pixel is classified into the five kinds of color groups and the number of the pixels is counted for each of the groups (ST24 to ST28). Also in this case, the steps ST26 to ST28 are skipped for a pixel having a gradation mean value Av which is smaller than the threshold L0.

When the processings for all the pixels in the inspection region are ended, a decision of "YES" is obtained at a step ST29 and the processing proceeds to a step ST32. At the step ST32, the number of the pixels obtained for each color group is compared with the decision reference value to decide the quality of the soldered portion.

On the other hand, in the case in which the portions other than the soldered portion are to be inspected, a decision of "NO" is obtained at the step ST23. At a step ST30, a shaded image in the inspection region is changed into a binary value based on a binary threshold for each color pattern so that color patterns for R, G and B are extracted. At a next step ST31, furthermore, the feature amount of each color pattern thus extracted is calculated and the processing then proceeds to a step ST32. At the step ST32, the feature amount thus calculated is compared with the decision reference value, thereby deciding the quality of the inspected portion.

In the same manner, subsequently, the image of each inspected portion is sequentially picked up and the inspection region is set based on the inspection information in the decision data file. Then, a decision processing using the number of the pixels for each color group is executed for the soldered portion and a decision processing using the feature amounts of three kinds of color patterns is executed for the portions other than the soldered portion.

When the decision processing for all the inspected portions is ended, a decision of "YES" is obtained at a step ST33. At steps ST34 to ST36, subsequently, it is decided whether the inspected substrate 1T is an excellent product or a defective product based on the result of the decision for each inspected portion. At a step ST37, furthermore, the result of the decision is output and the inspection for the inspected substrate 1T is thus ended.

In the substrate inspecting apparatus according to the present embodiment, thus, in the case in which the soldered portion is to be inspected, the distribution state of each color is decided by using the number of the pixels for five kinds of color groups corresponding to five kinds of colors in total including colors corresponding to the light sources 8, 9 and 10 and two kinds of mixed colors corresponding to the adjacent light sources. Therefore, it is possible to finely divide and detect the inclination angle of the soldered surface than that in the conventional art, thereby carrying out a detailed inspection.

In the processing of extracting each color component, moreover, one color component having a maximum intensity or the color component having a maximum intensity and a color component having the second highest intensity is/are extracted from three color components constituting image data for each pixel. Consequently, the inclination state of a solder surface in an image can be expressed by the five kinds of colors. In place of the automatic solder inspecting apparatus, accordingly, the processing of extracting the color component is executed in a visual inspecting apparatus and an image is displayed after the extraction processing. Consequently, it is possible to recognize, in detail, the inclination state of the soldered portion based on the distribution state of the five kinds of colors.

While the processing of extracting the color component is carried out on the basis of the mean value of the gradation of each color component in the embodiment described above, this is not restricted but the gradations of first and second color components may be compared with each other, only the first color component may be extracted if their difference is greater than a predetermined value, and the first and second color components may be extracted if the difference is equal to or smaller than the predetermined value.

In FIG. 2, the superior color components have the same size within the angle ranges A1, A2 and A3 in which the single color component is superior. Also within the angle range which can be detected with the same color, actually, a very small change is made depending on an angle.

Figure 11:
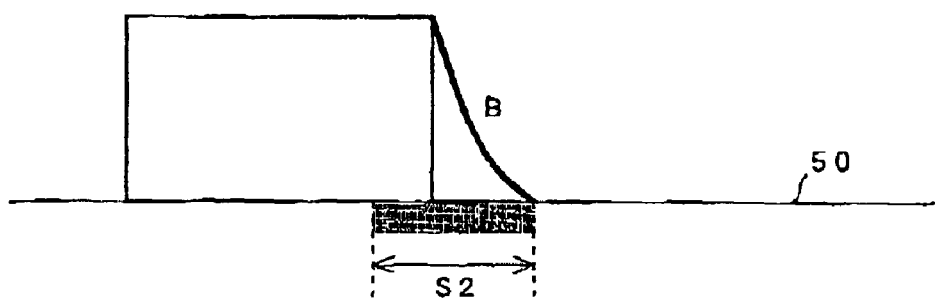
FIG. 11 is an explanatory view showing a result obtained in the case in which a steep surface is observed by the optical system in FIG. 8.

For example, the steep surface such as the fillet shown in FIG. 11 is detected as a blue pattern in the optical system shown in FIG. 1. In such an inclined surface, the blue component is gradually decreased from an upper part to a lower part.

For an inspection object in which a single color component is superior, accordingly, a plurality of thresholds can be set for the superior color component. According to such setting, it is possible to more finely divide and identify the angle range detected by one color in the conventional art. Referring to the steep surface, therefore, it is also possible to recognize the inclination state in detail, thereby carrying out an inspection with high precision. By reducing the set interval of the threshold, moreover, the resolution of the angle detection can be enhanced. Consequently, it is possible to detect a very small change in an angle with high precision.

Figure 7:
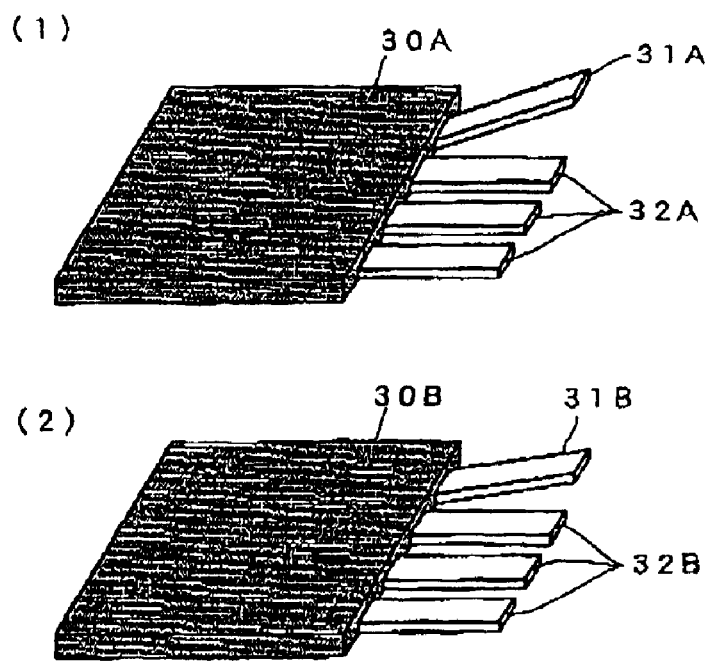
FIG. 7 is an explanatory view showing an example of an inspection object in which a plurality of thresholds are set to a detection range having the same color.
Figure 8:
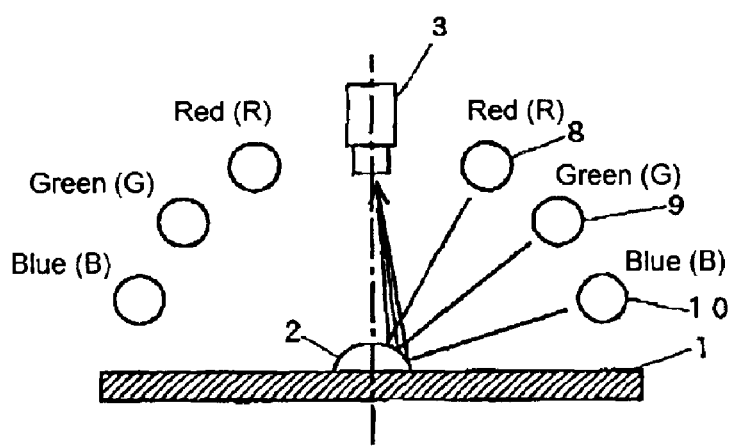
FIG. 8 is an explanatory view showing the structure of an optical system of a conventional substrate inspecting apparatus.
Figure 9:
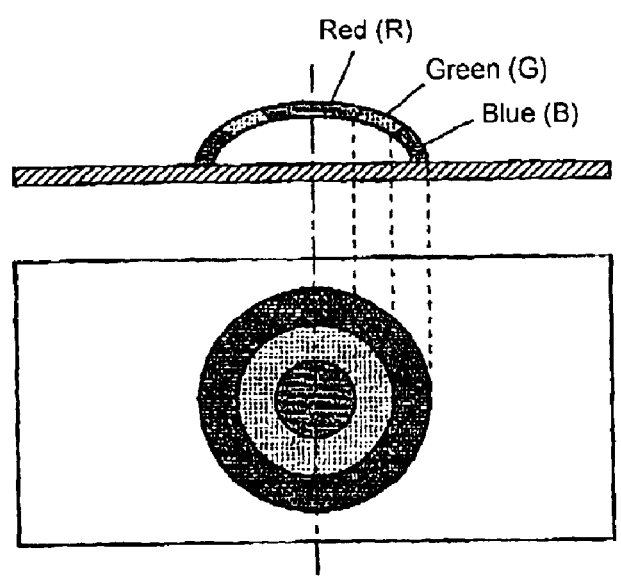
FIG. 9 is an explanatory view showing the principle of a recognizing process by the optical system in FIG. 8.
Figure 10:
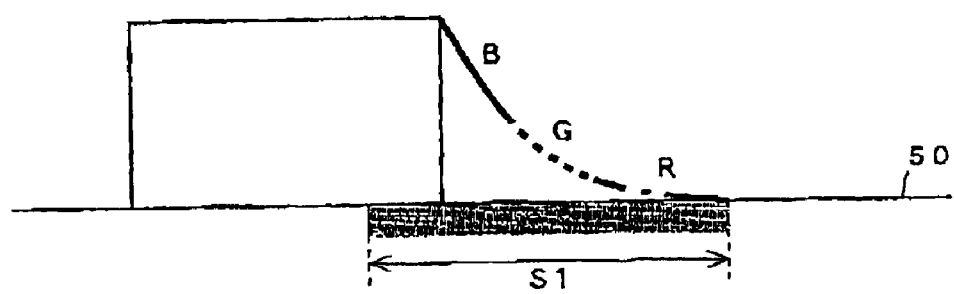
FIG. 10 is an explanatory view showing the principle of the recognizing process by the optical system in FIG. 8.

FIG. 7 shows an example of an inspection object in the case in which the state of an IC lead is to be inspected by using a plurality of thresholds set stepwise.

If a mounting state is proper, the upper surface of the lead is flat. Referring to the projecting section shown in FIG. 1, a lead on an image is represented by a red pattern. By setting a plurality of thresholds to a red component, accordingly, the inclination angle of the upper surface of the lead can be recognized finely.

FIG. 7(1) shows a state in which a float is generated on one lead 31A of a component 30A and FIG. 7(2) shows a state in which a very small float is generated on a lead 31B in the same position of the same component 30B. In FIGS. 7(1) and 7(2), 32A and 32B denote a lead in a good condition.

In the case in which the images of the leads 31A, 32A, 31B and 32B are picked up under an illumination by the projecting section 4 and red components indicative of the leads 31A and 31B are compared with each other over the images thus obtained, the red component in the lead 31A is smaller than that in the lead 31B. Moreover, when the red component corresponding to the defective lead 31B in FIG. 7(2) is compared with the red component corresponding to another excellent lead 32B, the former has a smaller value than the latter.

If three kinds of thresholds are set corresponding to the sizes of the red components indicative of the excellent leads 32A and 32B and the defective leads 31A and 31B, accordingly, a difference in an inclination between these leads can be detected with high precision.

In the case in which an inspection of this kind is to be carried out, the defective lead can be indicated by a color pattern corresponding to an inclination thereof if color patterns other than the red are caused to correspond to a threshold for detecting a defective lead. For example, if a green pattern is caused to appear when the inclination angle of the lead is comparatively great as shown in FIG. 7(1) and a yellow pattern is caused to appear when the inclination angle of the lead is very small as shown in FIG. 7(2), the inclination state of the lead can easily be decided based on these colors. Also in the example shown in FIG. 11, similarly, if thresholds in three stages are set to the blue component and the inclined surfaces detected by these thresholds are expressed in the color patterns of red, green and blue, for example, it is possible to carry out the same pattern display as that in the case of a gentle inclined surface.

The method of detecting an inclination angle based on a plurality of thresholds can be applied to the substrate inspecting apparatus shown in FIG. 1. If the method of changing a display color based on a detected angle is introduced into a visual inspecting apparatus having the same optical system as that in FIG. 1 in addition to the detecting method, moreover, a very small change in an inclination of an inspection object can easily be recognized visually so that an inspection can be carried out with high precision.

In both the automatic and visual apparatuses, furthermore, it is also possible to change over an inspection based on five kinds of color patterns corresponding to colors for the light sources and their mixed colors and an inspection for setting a plurality of thresholds to a single color component depending on the type of an inspected portion or the purpose of the inspection.

According to the present invention described above, in a color image obtained under an illumination in which a plurality of colored lights are irradiated in the directions of different elevation angles, inclined surfaces adapted to the colored lights and an inclined surface in the boundary position of the inclined surfaces are extracted based on the different colors by a processing of extracting one color component having a maximum intensity in a color component corresponding to each colored light and a processing of extracting the color component having a maximum intensity and a color component having the second highest intensity. Consequently, it is possible to enhance a resolution related to the detection of the inclination angle by the optical system having the same structure as that of the conventional art.

In the present invention, referring to the inclination angle range detected by the same color, a color component constituting the color is compared with a plurality of thresholds which are set stepwise. Consequently, it is possible to enhance a resolution related to the detection of the inclination angle by the optical system having the same structure as that of the conventional art.

In the present invention, therefore, it is possible to divide and detect the inclination angle of a steep surface and to detect a fine change in an angle of the surface with high precision. With the same hardware structure as that of the conventional art, consequently, it is possible to enhance precision in an inspection related to the surface state of an inspection object.

What is claimed is:

1. A surface state inspecting method comprising the steps of:

picking up an image of a light reflected from an inspection object under an illumination condition in which different colored lights are irradiated in a plurality of directions having different elevation angles with respect to the inspection object;

selecting and executing a processing of extracting one color component having a maximum intensity in color components corresponding to the colored lights or a processing of contracting the color component having a maximum intensity and a color component having the second highest intensity for each pixel in an image reqion including an image of the inspection object based on a relationship between the intensities of the color components with respect to the image obtained by the image pick-up; and inspecting a surface state of the inspection object by using image data indicative of a result of the processing of extracting a color component in the image region.

2. The surface state inspecting method according to claim 1, wherein the colored lights emitted in the directions have red, green and blue colors and the step of the processing of extracting a color component includes the step of obtaining a mean value of the intensities of the color components and the step of extracting one or two color components which is/are greater than the mean value.

3. The surface state inspecting method according to claim 1, wherein the step of inspecting a surface state of the inspection object includes the step of grouping each pixel in the region based on a type and combination of an extracted color component in the pixel region after executing the step of the processing of extracting a color component, and the step of deciding a suitability of the surface state of the inspection object based on a distribution state of a pixel belonging to each group.

4. A substrate inspecting apparatus comprising:

illuminating means having a plurality of light sources for emitting different colored lights which are provided in directions of different elevation angles with respect to a substrate to be an inspection object, respectively;

image pick-up means for picking up an image of a light reflected from the substrate;

image input means for fetching an image generated by the image pick-up means in a state in which each of the light sources of the illuminating means is turned on;

color component extracting means for selecting and executing a processing of extracting one color component having a maximum intensity in color components corresponding to the light sources or a processing of extracting the color component having a maximum intensity and a color component having the second highest intensity based on a relationship of an intensity of each color component for each pixel in an image region including an image of the inspection object with respect to the input image fetched by the image input means;

deciding means for deciding a suitability of a surface state of the inspection object by using image data in the image region after executing the processing by the color component extracting means; and output means for outputting a result of the decision carried out by the deciding means.

5. The substrate inspecting apparatus according to claim 4, wherein the illuminating means includes three kinds of light sources for emitting colored lights of red, green and blue, and the color component extracting means includes means for calculating a mean value of the intensities of the color components corresponding to each of the light sources and means for extracting one or two color components which is/are greater than the mean value thus calculated.

6. The substrate inspecting apparatus according to claim 4, wherein the deciding means includes means for grouping each pixel in the image region based on a type and combination of the extracted color component after the processing of the color component extracting means, thereby deciding a suitability of a surface state of the inspection object based on a distribution state of a pixel belonging to each group.

7. A substrate inspecting apparatus comprising:

illuminating means having a plurality of light sources for emitting different colored lights which are provided in directions of different elevation angles with respect to a substrate to be an inspection object, respectively;

image pick-up means for picking up an image of a light reflected from the substrate;

image input means for fetching an image generated by the image pick-up means in a state in which each of the light sources of the illuminating means is turned on;

color component extracting means for selecting and executing a processing of extracting one color component having a maximum intensity in color components corresponding to the light sources or a processing of extracting the color component having a maximum intensity and a color component having the second highest intensity based on a relationship of an intensity of each color component for each pixel, in an image region including an image of the inspection object with respect to the input image fetched by the image input means;

display means for displaying an image by each color component extracted by the color component extracting means; and input means for accepting an input of data indicative of a result of a decision of quality for the image displayed by the display means.

* * * * *